(12) United States Patent
Kakutani et al.

(10) Patent No.: US 9,386,683 B2
(45) Date of Patent: Jul. 5, 2016

(54) PARTICLE ACCELERATOR AND MEDICAL EQUIPMENT

(71) Applicant: Kabushiki Kaisha Toshiba, Minato-ku (JP)

(72) Inventors: Akiko Kakutani, Kanagawa (JP); Kiyokazu Sato, Tokyo (JP); Takeshi Yoshiyuki, Kanagawa (JP); Takashi Yazawa, Tokyo (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 82 days.

(21) Appl. No.: 14/171,910

(22) Filed: Feb. 4, 2014

(65) Prior Publication Data

US 2014/0243576 A1  Aug. 28, 2014

(30) Foreign Application Priority Data

Feb. 22, 2013  (JP) .................. 2013/033212

(51) Int. Cl.
*A61N 5/10* (2006.01)
*H05H 13/04* (2006.01)

(52) U.S. Cl.
CPC ............. *H05H 13/04* (2013.01); *A61N 5/1077* (2013.01); *A61N 2005/1088* (2013.01)

(58) Field of Classification Search
USPC ........................................................ 315/500
See application file for complete search history.

(56) References Cited

U.S. PATENT DOCUMENTS

| | | | | |
|---|---|---|---|---|
| 7,939,809 B2* | 5/2011 | Balakin | ..................... | A61N 5/10 250/396 R |
| 8,067,748 B2* | 11/2011 | Balakin | ................ | A61N 5/1049 250/396 ML |
| 8,222,617 B2* | 7/2012 | Iseki | ..................... | A61N 5/1043 250/396 ML |
| 8,624,528 B2* | 1/2014 | Balakin | ..................... | A61N 5/10 250/396 R |
| 8,841,866 B2* | 9/2014 | Balakin | ................... | G21K 1/087 315/500 |
| 8,933,415 B2* | 1/2015 | Kakutani | ............. | A61N 5/1077 250/423 P |

(Continued)

FOREIGN PATENT DOCUMENTS

| | | |
|---|---|---|
| CN | 102387836 A | 3/2012 |
| CN | 102793979 A | 11/2012 |

(Continued)

OTHER PUBLICATIONS

Combined Office Action and Search Report issued on Dec. 28, 2015 in Chinese Patent Application No. 201410059273.3 with English translation of category of cited documents.

*Primary Examiner* — Douglas W Owens
*Assistant Examiner* — Srinivas Sathiraju
(74) *Attorney, Agent, or Firm* — Oblon, McClelland, Maier & Neustadt, L.L.P.

(57) ABSTRACT

One embodiment of a particle accelerator includes: a particle source from which a particle beam is extracted with a beam pulse width of not greater than 2 μsec; a linear accelerator for accelerating the particle beam extracted from the particle source; a synchrotron for receiving the particle beam transported thereto from the linear accelerator and causing the particle beam to circulate in order to accelerate it until it gets to a predetermined energy level; a bump electromagnet for shifting the circulating path of the particle beam each time it makes a full turn; and a control unit for controlling the extent of magnetic excitation of the bump electromagnet and for controlling the timing of magnetic excitation of the bump electromagnet according to the pulse timing of the particle source.

9 Claims, 7 Drawing Sheets

(56) References Cited

U.S. PATENT DOCUMENTS

| | | | | |
|---|---|---|---|---|
| 9,018,601 B2* | 4/2015 | Balakin | | A61N 5/1049 |
| | | | | 250/396 ML |
| 9,095,040 B2* | 7/2015 | Balakin | | H05H 7/10 |
| 2009/0091817 A1* | 4/2009 | Jennings | | H01L 21/67115 |
| | | | | 359/298 |
| 2009/0309046 A1* | 12/2009 | Balakin | | A61N 5/1049 |
| | | | | 250/492.3 |
| 2010/0080356 A1* | 4/2010 | Ishida | | G21K 1/087 |
| | | | | 378/121 |
| 2010/0127183 A1* | 5/2010 | Iseki | | A61N 5/1043 |
| | | | | 250/396 ML |
| 2010/0207552 A1* | 8/2010 | Balakin | | A61N 5/10 |
| | | | | 315/503 |
| 2011/0313232 A1* | 12/2011 | Balakin | | A61N 5/10 |
| | | | | 600/1 |
| 2012/0143051 A1* | 6/2012 | Balakin | | A61N 5/1049 |
| | | | | 600/427 |
| 2012/0242257 A1* | 9/2012 | Balakin | | H05H 13/04 |
| | | | | 315/503 |
| 2013/0193353 A1* | 8/2013 | Ikeda | | H05H 13/04 |
| | | | | 250/492.3 |

FOREIGN PATENT DOCUMENTS

| | | |
|---|---|---|
| EP | 0 700 236 A1 | 3/1996 |
| JP | 5-166599 A | 7/1993 |
| JP | 5-198398 A | 8/1993 |
| JP | 2596292 | 4/1997 |
| JP | 3246364 | 1/2002 |
| JP | 2009-217938 | 9/2009 |
| JP | 2012-99273 | 5/2012 |

* cited by examiner

PARTICLE ACCELERATOR AND MEDICAL EQUIPMENT

CROSS REFERENCE TO RELATED APPLICATION

This application is based upon and claims the benefit of priority from Japanese Patent Application No. 2013-33212, filed on Feb. 22, 2013, the entire content of which is incorporated herein by reference.

FIELD

Embodiments described herein relate to a particle accelerator for accelerating a particle beam and also to medical equipment using the same.

BACKGROUND

Particle accelerators for accelerating ions and protons are being widely utilized for physical experiment and cancer therapy apparatus. The related background art for the present invention will be described below in terms instances where a particle accelerator is employed for the cancer therapy apparatus. Proton beams and heavy particle beams are being employed for cancer therapy. More specifically, the related background art will be described below in terms of heavy particle beams. Heavy particle beams are mainly formed by carbon ions. Carbon ions are generated from an ion source and accelerated by a plurality of accelerators before they are irradiated onto the diseased part of a patient (see, for example, Japanese Patent Application Laid-Open Publication No. 2009-217938, Japanese Patent Publication No. 2,596,292 and Japanese Patent Publication No. 3,246,364 the entire contents of which are incorporated herein by reference).

An ion accelerator comprises as main components thereof an ion source, a linear accelerator (radio frequency quadrupole type linear accelerator, to be referred to as RFQ hereinafter), a drift tube type linear accelerator (drift tube LINAC, to be referred to as DTL hereinafter), a beam transport system and a synchrotron.

In conventional ion accelerators for cancer therapy, quadrivalent carbon ions ($C^{4+}$) are generated in an electron cyclotron resonance (to be referred to as ECR hereinafter) ion source. The generated quadrivalent carbon ions are accelerated to get to an energy level of several MeV/u by a linear accelerator and subjected to charge conversion in a charge converter to become hexavalent carbon ions ($C^{6+}$). The hexavalent carbon ions ($C^{6+}$) are then injected into a synchrotron so as to be accelerated by the synchrotron.

Essentially, linear accelerators show a high acceleration efficiency when they use hexavalent carbon ions ($C^{6+}$). However, conventional ECR ion sources cannot reliably provide the amperage of hexavalent carbon ions ($C^{6+}$) that is required for cancer therapy. Therefore, conventional ECR ion sources use quadrivalent carbon ions ($C^{4+}$).

The ion beam coming out from the ECR ion source is a DC beam and there is an upper limit amperage for the ion beam that can be extracted from an ion source (currently several hundred μA). For this reason, a so-called multi-turn injection technique is employed to inject an ion beam into a synchrotron to secure the number of ions necessary for cancer therapy.

Meanwhile, single turn injection and multi-turn injection are known to date as techniques for injecting an ion beam into a synchrotron. With the single turn injection technique, the number of ions necessary for cancer therapy is injected with a one-time injection. On the other hand, the multi-turn injection technique is a technique of securing the number of ions necessary for cancer therapy by causing injected ions to travel along a circulating path and injecting additional ions for a plurality of times.

However, when injecting a beam after the circulation time (about 2 μsec) is over, there arises a problem that the newly injected ions cannot follow the path of the ion beam that has made a full turn once. To avoid this problem, the circulating path of the ion beam in the synchrotron is shifted by using a bump magnet to make the path vary with time and allow additional ion beam injections for a plurality of times.

Besides, for accelerator systems that are currently popularly being operated in Japan, the optimum energy for converting carbon quadrivalent ions ($C^{4+}$) into carbon hexavalent ions ($C^{6+}$) is 4 MeV/u so that the level of acceleration energy in linear accelerators is determined.

Meanwhile, a large electric current can be extracted from a laser ion source although only with short pulses (up to several μsec). A laser ion source is an apparatus designed to condense a laser beam, irradiating it onto a target and, evaporating and ionizing the target element by means of the energy of the laser beam to generate plasma. The ions contained in the plasma are transported as plasma ions and accelerated when they are extracted to produce an ion beam (see, for example, Japanese Patent Application Laid-Open Publication No. 2012-99273 the entire content of which is incorporated herein by reference).

A laser ion source can produce an ion beam by irradiating a laser beam onto a target and generate ions. It is advantageous for generating a high current multivalent ion beam. Reports say that hexavalent carbon ions ($C^{6+}$) generated by laser ion sources can produce peak electric currents in the order of several mA with a pulse width up to 2 μsec in synchronism with the timing of laser irradiation. The result corresponds to the number of ions with which the synchrotron of a cancer therapy can provide the required amperage in a single pulse.

Now, a known ion accelerator will be described below by referring to FIG. 7.

Figure 7:
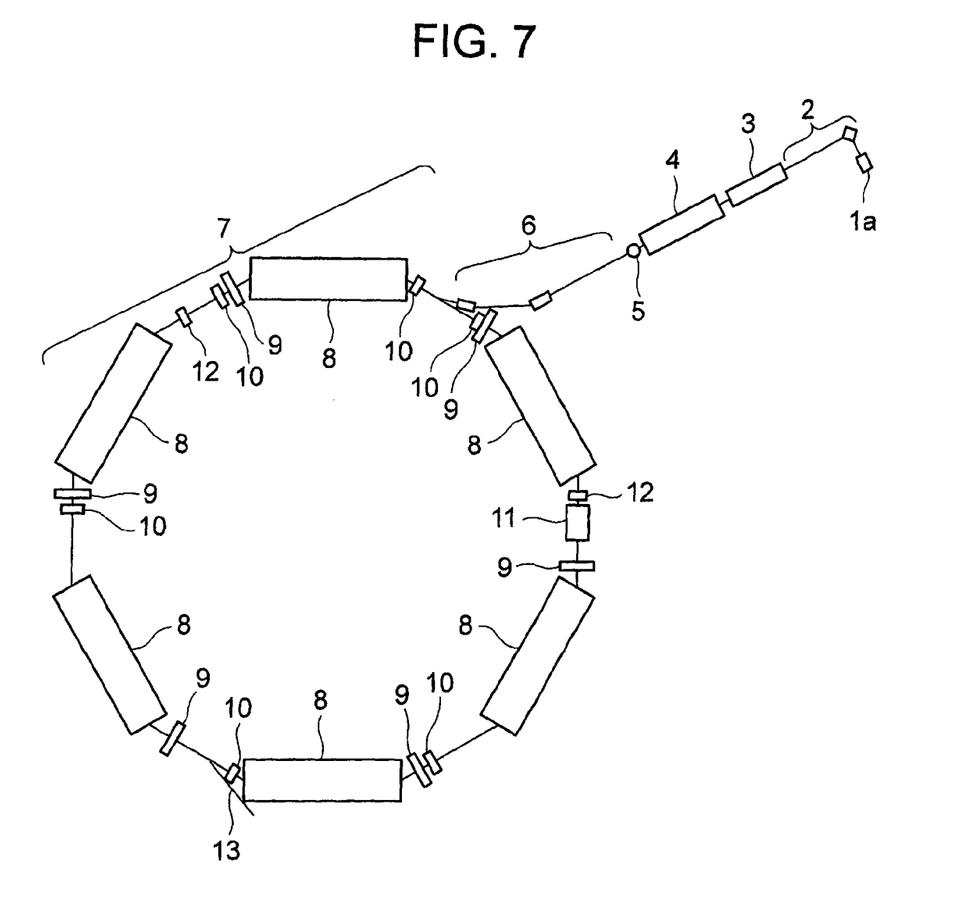
FIG. 7 is a known particle accelerator, showing the configuration thereof.

As shown in FIG. 7, the ions generated by an ion source 1 are transported by means of a low energy beam transport system (to be referred to as LEBT system hereinafter) 2 to an RFQ 3 and a DTL 4, which are linear accelerators arranged downstream, while the beam characteristics thereof are regulated by the LEBT system 2. A known technique of causing electric discharge to occur in gas to obtain ions is employed for the ion source 1. A microwave or an electron beam is utilized to cause electric discharge to occur.

Generally, ECR ion sources are employed in accelerators for cancer therapy. ECR ion sources are designed to ionize gas in order to generate plasma and extract ions by means of an electric field. The extraction current is a direct current. While ECR ion sources can generate multivalent ions, high valent ions show only a small amperage value. Therefore, the ECR ion source generates quadrivalent carbon ions ($C^{4+}$) in order to secure the ion amperage required for cancer therapy and then accelerate the carbon ions by means of the RFQ 3 and the DTL 4.

The ions emitted from the DTL 4 are converted from quadrivalent carbon ions ($C^{4+}$) to hexavalent carbon ions ($C^{6+}$) by a charge converter 5 and transported into a synchrotron 7 by way of middle energy beam transport system (to be referred to MEBT system hereinafter) 6.

The synchrotron 7 comprises deflector electromagnets 8, quadrupole electromagnets 9, hexapole electromagnets 10 and a radio frequency accelerating cavity 11. Although not shown, the synchrotron 7 additionally comprises a correcting magnet and monitors for monitoring ion beams. After the ion beam is accelerated to get to a satisfactory energy level, it is transported to an irradiation room (not shown) by way of an injection path 13 that passes a bump electromagnet 12 for ion beam injection and a septum electromagnet (not shown) and irradiated to the diseased part of a patient for cancer therapy.

Generally, the ion beam that is injected into the synchrotron 7 is provided with an injection path prepared by using the bump electromagnet 12 for ion beam injection that is arranged in the synchrotron 7 for the purpose of multi-turn injection.

Figure 8:
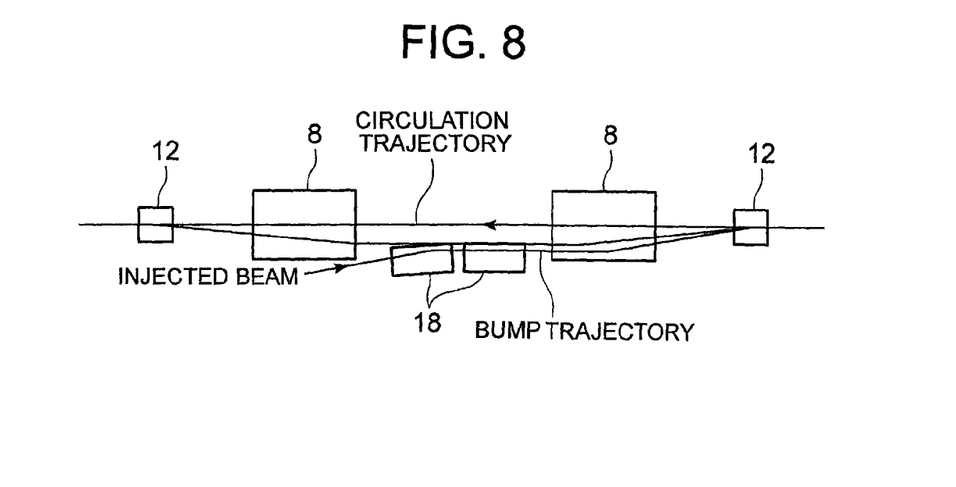
FIG. 8 is a schematic illustration of a known multi-turn injection method.

Conventional multi-turn injection method will be described below in terms of proton beam multi-turn injection that disclosed in OHO '87 High-energy Accelerator Seminars shown in FIG. 8. As shown in FIG. 8, the bump electromagnet 12 for ion beam injection shifts the path each time the ion beam makes a full turn. The ion beam is forced to make full turns by way of the deflector electromagnets 8, the quadrupole electromagnets 9, the hexapole electromagnets 10 and the septum magnet 18 that are the magnets of the synchrotron so as to be accelerated to a predetermined energy level.

Figure 9:
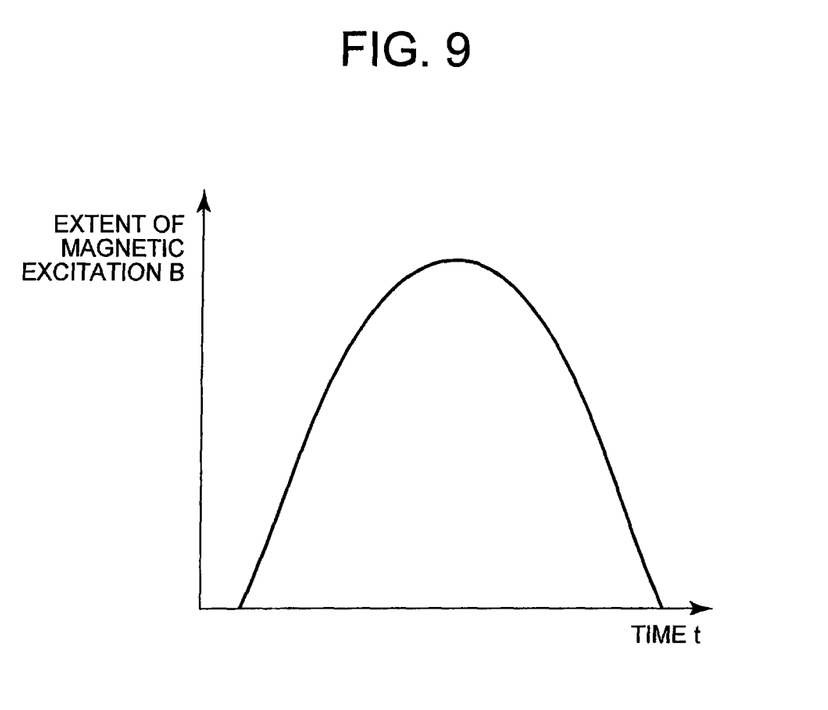
FIG. 9 is a graph illustrating the magnetic excitation waveform of the bump magnet of FIG. 8.

The magnetic excitation waveform of the bump electromagnet 12 is shown in FIG. 9. Ion beam injections are conducted at the side where the extent of magnetic excitation falls. While the magnetic excitation width depends on the ring circulation time in the synchrotron 7, it is in the order up to several hundred µsec. Therefore, the ion current that is generally employed for injection is subjected to chopping (of removing the beam that becomes unnecessary for a certain period) before being injected into the RFQ 3 in synchronism with bump excitation time.

As described above, since the highest amperage value of the electric current of the particle source for a particle accelerator in a synchrotron is relatively small, the number of particles necessary for cancer therapy or a physical experiment is obtained by means of multi-turn injection.

For this reason, conventional particle accelerators face a problem that it is difficult for them to raise the amperage value of the circulating current. It is difficult in the current status of technology to remarkably raise the amperage value of the circulating current although it is desired for scanning irradiations and other applications.

A remarkable improvement can be expected for the amperage value of the circulating current when the technique of multi-turn injection using a short pulse particle source showing a large highest peak current value such as a laser ion source is employed. However, since the pulse width of the laser ion source is equal to or smaller than the synchrotron circulation time, it has not been possible to realize multi-turn injection with the conventional method.

Therefore, the object of the present embodiment is to provide a particle accelerator for which the amperage value of the circulating current can be raised and the particle beam utilization efficiency can be improved and also provide medical equipment using such a particle accelerator in order to solve the above-identified problem.

BRIEF DESCRIPTION OF THE DRAWINGS

The features and advantages of the present invention will become apparent from the discussion hereinbelow of specific, illustrative embodiments thereof presented in conjunction with the accompanying drawings, in which.

DETAILED DESCRIPTION

According to one embodiment, there is provided a particle accelerator comprising: a particle source from which a particle beam is extracted with a beam pulse width of not greater than 2 µsec such as a laser ion source for extraction of an ion beam from the plasma generated therein by irradiation of a laser beam; a linear accelerator for accelerating the particle beam extracted from the particle source; a synchrotron for receiving the particle beam transported thereto from the linear accelerator and causing the particle beam to circulate in order to accelerate it until it gets to a predetermined energy level; a bump magnet for shifting the circulating path of the particle beam each time it makes a full turn; a control unit for controlling the extent of magnetic excitation of the bump magnet and for controlling the timing of magnetic excitation of the bump magnet according to the pulse timing of the particle source.

Further, according to another embodiment, there is provided medical equipment comprising: a particle source from which a particle beam is extracted with a beam pulse width of not greater than 2 µsec; a linear accelerator for accelerating the particle beam extracted from the particle source; a synchrotron for receiving the particle beam transported thereto from the linear accelerator and causing the particle beam to circulate in order to accelerate it until it gets to a predetermined energy level; a bump magnet for shifting the circulating path of the particle beam each time it makes a full turn; a control unit for controlling the extent of magnetic excitation of the bump magnet and for controlling the timing of magnetic excitation of the bump magnet according to the pulse timing of the particle source such as the pulse timing of the laser beam; a takeout device for taking out the particle beam accelerated by the synchrotron; and an irradiation device for irradiating the particle beam taken out by the takeout device onto an object of irradiation.

Now, embodiments of particle accelerators according to the present invention will be described in greater detail by referring to the accompanying drawings. The embodiments of particle accelerators that will be described hereinafter are those that are applied to cancer therapy equipment as medical devices.

First Embodiment

Figure 1:
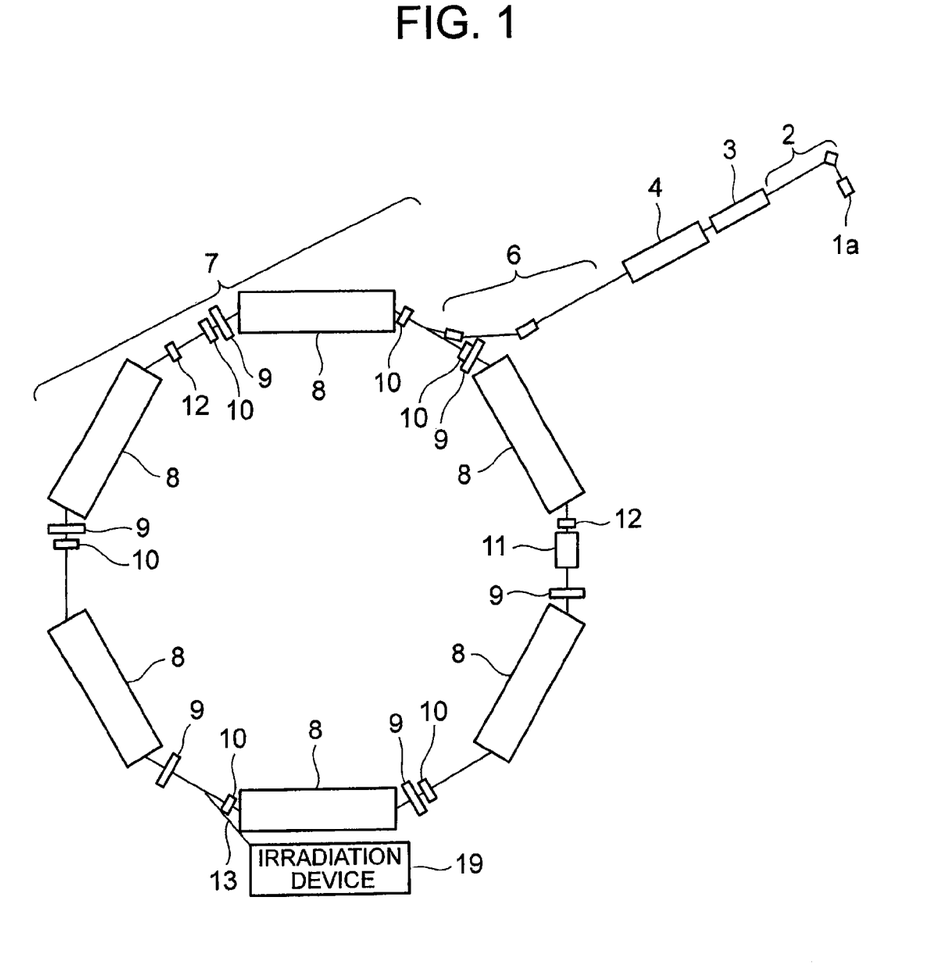
FIG. 1 is a schematic illustration of the first embodiment of a particle accelerator according to the present invention, showing the configuration thereof.
Figure 2:
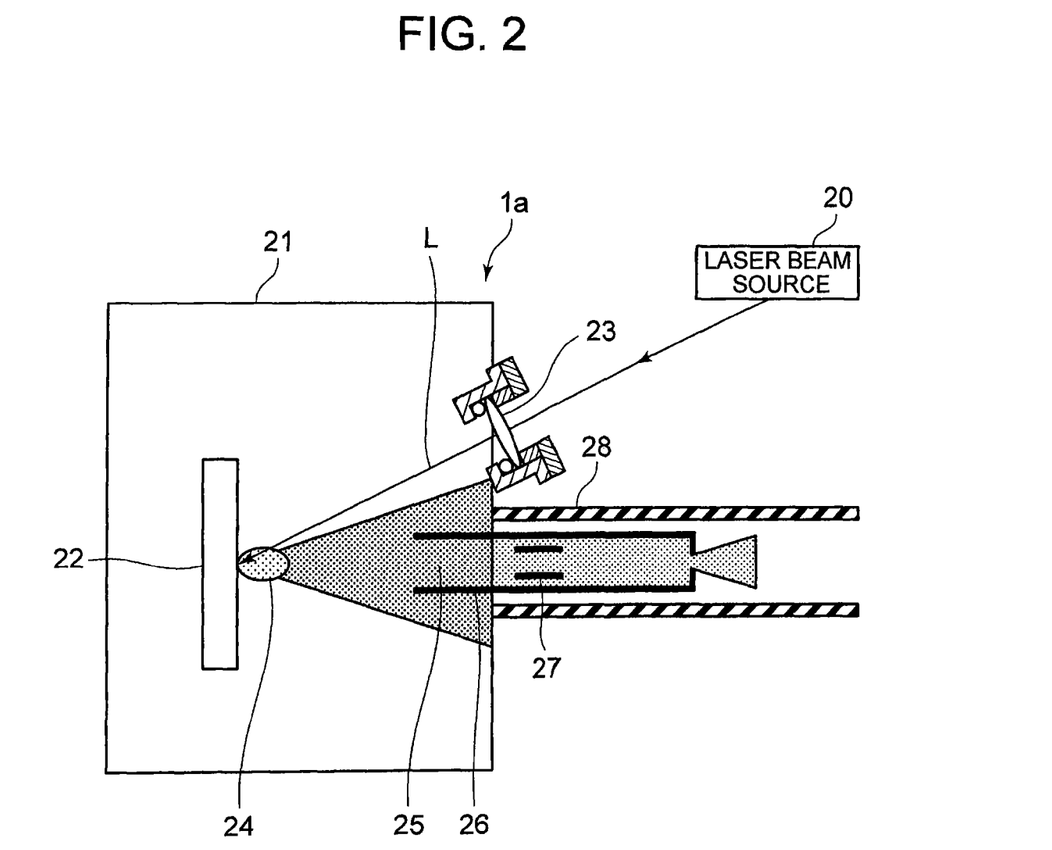
FIG. 2 is a schematic cross-sectional view of the laser ion source of FIG. 1, showing the configuration thereof.

FIG. 1 is a schematic illustration of the first embodiment of a particle accelerator according to the present invention, showing the configuration thereof. FIG. 2 is a schematic cross-sectional view of the laser ion source of FIG. 1, showing the configuration thereof. Note that the components same as those of the known ion accelerator shown in FIG. 7 are denoted respectively by the same reference symbols. Also note that the septum magnet of this embodiment is omitted from the drawings.

Roughly speaking, as shown in FIG. 1, the ion accelerator of this embodiment has a laser ion source 1a, which is, a particle source, an RFQ 3, a DTL 4, a RFQ 3 and the DTL 4 being linear accelerators, a LEBT system 2, a MEBT system 6, a LEBT system 2 and the MEBT system being beam transport systems, a synchrotron 7 and a bump electromagnet 12. The laser ion source 1a, the linear accelerators including the RFQ 3 and the DTL 4, and the LEBT system 2, which is a beam transport system, constitute an injector. As described above, particles are extracted with a beam pulse width of not greater than 2 μsec from the laser ion source 1a.

The ions generated in the laser ion source 1a are transported to the RFQ 3 and the DTL 4 that are arranged downstream of the laser ion source 1a, while the beam characteristics thereof are regulated by the LEBT system 2. The RFQ 3 electrically converges and accelerates the ion beam. The DTL 4 electrically accelerates the ion beam. The ion beam emitted from the DTL 4 is transported to the synchrotron 7 by way of the MEBT system 6.

The synchrotron 7 is an apparatus for further accelerating the ion beam by making it circulate for a plurality of times until it gets to an energy level required for cancer therapy. More specifically, the synchrotron 7 comprises the deflector electromagnets 8 for forming circulating paths, the quadrupole electromagnets 9 for controlling the convergence of the ion beam, the hexapole electromagnets 10 for correcting chromaticity (chromatic aberration) and the radio frequency accelerating cavity 11 for accelerating the ion beam.

The ion beam is accelerated to get to a satisfactory energy level by the synchrotron 7, and subsequently transported to an irradiation room (not shown) from emission trajectory 13 by way of the bump electromagnet 12 for emission and a take-up device 17 shown in FIG. 3 so as to be irradiated onto the diseased part of a patient, which is the target of irradiation, by means of a irradiation device 19 in a irradiation room for cancer therapy.

Now, the configuration of the laser ion source 1a of this embodiment will be described in detail by referring to FIG. 2.

As shown in FIG. 2, the laser ion source 1a has a vacuum container 21. A target 22, which may be a mass of an element that turns into ions or a material containing such an element, is arranged in the inside of the vacuum container 21. The target 2 typically is a carbon-based plate-shaped member.

A condenser lens 23 is fitted to a laser beam entrance window for allowing the laser beam to enter, the laser beam entrance window being arranged at an upper part of a lateral surface of the vacuum container 21. The condenser lens 23 is for condensing the laser beam L onto the target 22. The laser beam L emitted from a laser beam source 20 enters the vacuum container 21 through the condenser lens 23 and then condensed and irradiated onto the target 22. For example, a $CO_2$ laser or an Nd-YAG laser can be used for the laser beam source 20.

A transport pipe 28 for taking out ions is arranged at a lateral surface (at the right lateral surface in FIG. 1) of the vacuum container 21. Extraction electrodes 26 are arranged in the transport pipe 28 to eliminate unnecessary ions by applying a positive electric field.

The laser ion source 1a having the above described configuration condenses the laser beam L emitted from the laser beam source 20, which is pulse-driven, by means of the condenser lens 24 and irradiates it onto the target 22. A minute portion of the target 22 is heated by the laser beam L to high temperatures at the focal point on the target 22 where the laser beam L is focused. The portion that is heated to high temperatures turns into plasma, which is referred to as laser ablation plasma 24.

The laser ablation plasma 24 is transported through the transport pipe 28 having a high positive electric potential, and only necessary ions 25 are accelerated due to the potential difference between the transport pipe 28 and the RFQ 3 and the DTL4, which are linear accelerators at the ground potential, to become an ion beam. This ion beam is made to enter the RFQ 3 and the DTL 4. Unnecessary ions are eliminated by the electrodes 27.

Now, the control system of the particle accelerator of this embodiment will be described below.

Figure 3:
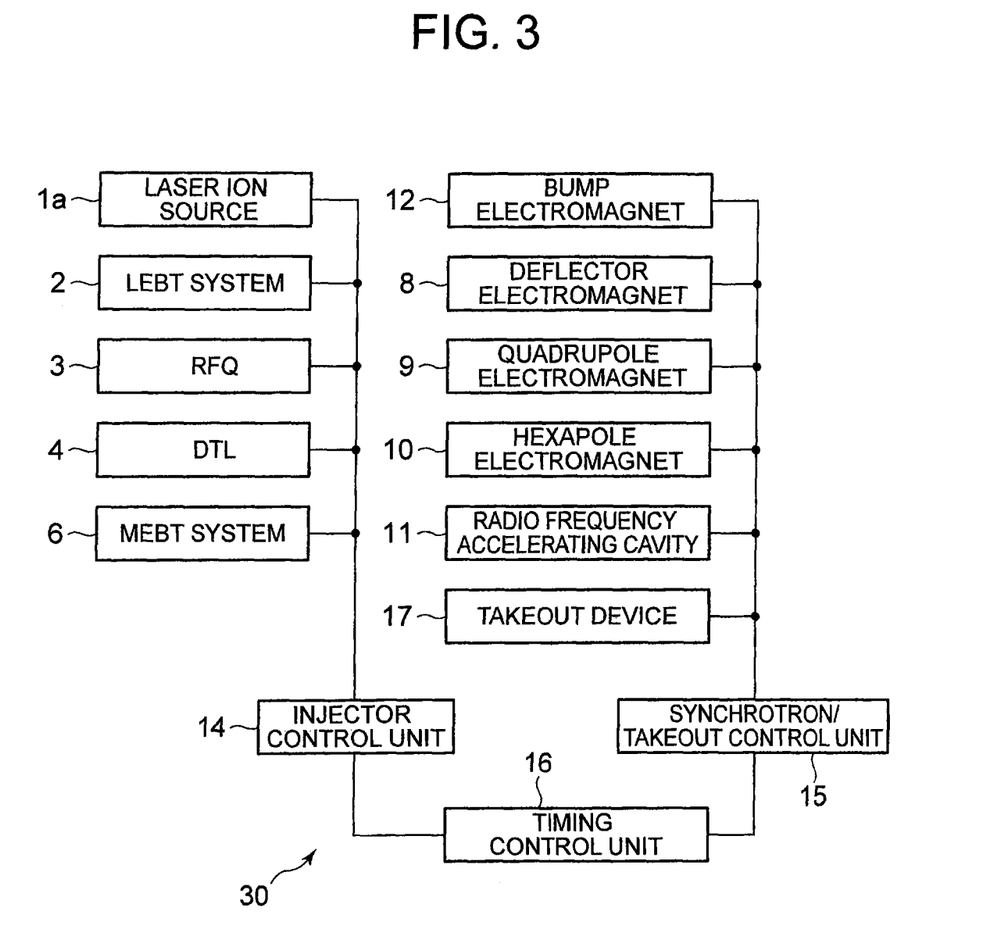
FIG. 3 is a schematic block diagram of the control system of the first embodiment.
Figure 4:
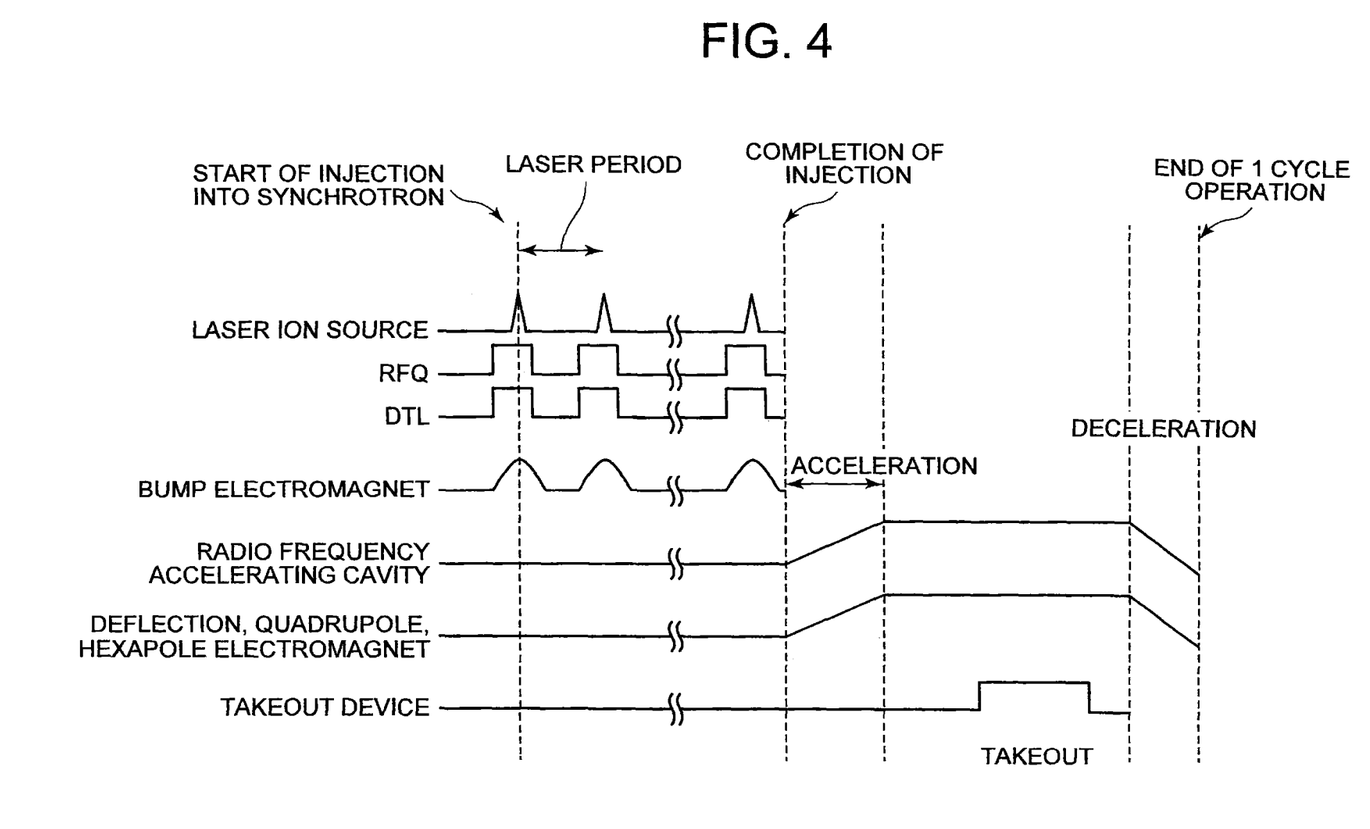
FIG. 4 is a timing chart for the operations of different sections in FIG. 3.
Figure 5:
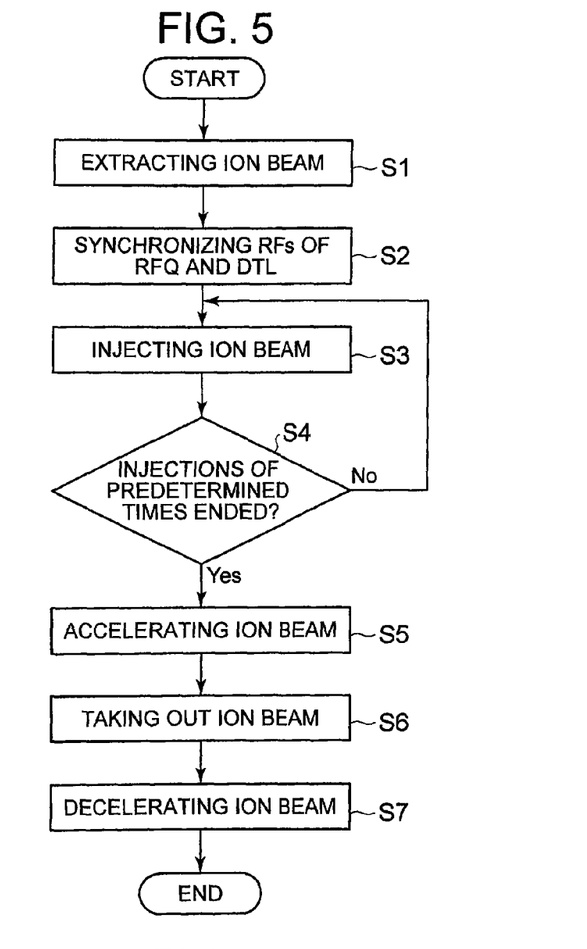
FIG. 5 is a flowchart of the operations of different sections in FIG. 3.

FIG. 3 is a schematic block diagram of the control system of the first embodiment. FIG. 4 is a timing chart for the operations of different sections in FIG. 3. FIG. 5 is a flowchart of the operations of different sections in FIG. 3.

As shown in FIG. 3, a control unit 30 has, for example, an injector control unit 14, a synchrotron/takeout control unit 15, and a timing control unit 16. The injector control unit 14 electrically controls the laser ion source 1a, the LEBT system 2, the RFQ 3, the DTL 4 and the MEBT system 6. More specifically, the injector control unit 14 controls the voltages and the electric currents of the power supplies of the magnets of the LEBT system 2 and the MEBT system 6, the electric currents and the voltages of the radio frequency power supplies of the RFQ 3 and the DTL 4, the voltage and the electric current of the power supply of the laser beam source 20 and the voltage and the electric current of the high voltage DC power supply, while it also monitors the degrees of vacuum of the above listed components and the soundness of the beam monitors.

The synchrotron/takeout control unit 15 electrically controls the bump electromagnet 12, the deflector electromagnets 8, the quadrupole electromagnets 9, the hexapole electromagnets 10, the radio frequency accelerating cavity 11 and the takeout device 17. To be more specific, the synchrotron/takeout control unit 15 controls the power supplies of the magnets of the above listed components and the voltage and the electric current of the radio frequency power supply, while it also monitors the degrees of vacuum of the above listed components and the soundness of the beam monitors. The synchrotron/takeout control unit 15 of this embodiment regulates the extent of magnetic excitation of the bump electromagnet 12 by controlling the electric current of the bump electromagnet 12 at each injection.

The timing control unit 16 controls the output timings of the laser beam source power supply of the laser ion source 1a, the radio frequency power supply of the RFQ 3, the radio frequency power supply of the TDL 4, the power supply of the bump electromagnet 12, the radio frequency power supply of the radio frequency accelerating cavity 11, the power supplies of the deflector electromagnets 8 and the quadrupole electromagnets 9 and the hexapole electromagnets 10 of the synchrotron 7, and the power supply of the takeout device 17. The timing control unit 16 of this embodiment controls the timing of magnetic excitation of the bump electromagnet 12 according to the pulse timing of the laser ion source 1a.

Now the operations of the control systems of this embodiment will be described by referring to FIGS. 4 and 5.

As shown in FIGS. 4 and 5, firstly the ion beam of several μsec is extracted by laser irradiation of the laser ion source 1a (Step S1). More specifically, the ion beam drawn out from the laser ion source 1a has a repetition frequency that is synchronized with the laser irradiation timing. The pulse width of the ion beam depends on the ion velocity in the plasma and the distance from the laser ion source 1a to the extraction electrodes 26.

Generally, a pulse width between several hundred nsec and 2 μsec is required for generating hexavalent carbon ions ($C^{6+}$) necessary for cancer therapy. Laser ion sources are characterized by a high peak current because the plasma source of the laser ion source is solid and hence the plasma density is high if compared with ECR ion sources that employ gas.

Then, the timing control unit 16 synchronizes the output of the radio frequency (RF) power supply of the RFQ 3 and that of the radio frequency (RF) power supply of the DTL 4 so as to accelerate the ion beam of the laser ion source 1a (Step S2).

Thereafter, the bump electromagnet 12 is magnetically excited with the output timing of the power supply thereof synchronized with the laser ion source 1a and the ion beam is injected into the synchrotron 7 (Step S3).

Subsequently, the ion beam is injected repeatedly into the synchrotron 7 such that the ion beam makes full turns for a predetermined number of times, which may be 10 times for example (Step S4).

If the injected ion beam has made full turns for the predetermined number of times in Step S4 (Step S4: Yes), the process proceeds to Step S5.

In Step S5, the output timing of the radio frequency power supply of the radio frequency accelerating cavity 11 and the output timings of the magnet power supplies of the deflector electromagnets 8, the quadrupole electromagnets 9 and the hexapole electromagnets 10 are synchronized to accelerate the ion beam until it gets to the energy level required for cancer therapy.

After the end of the ion beam acceleration process, the ion beam is taken out by the takeout device 17 (Step S6) and transported to the irradiation room (not illustrated) from an emission trajectory 13. Then, the ion beam is irradiated onto the target diseased part of the patient in the irradiation room by means of the irradiation device 19 for cancer therapy.

In Step S7, the output timing of the radio frequency power supply of the radio frequency accelerating cavity 11 and those of the power supplies of the deflector electromagnets 8, the quadrupole electromagnets 9 and the hexapole electromagnets 10 are synchronized to decelerate the ion beam. The operation of the particle accelerator is terminated after the above described operation sequence is over.

Now, the effect of the above described multi-turn injection of Step S4 will be described below.

With known multi-turn techniques, the bump electromagnet 12 is magnetically excited and a laser beam is injected by utilizing a fall of the intensity of the magnetic field. At this time, since the ion beam from the ion source is a DC ion beam, it is injected into the synchrotron 7 as DC, following the change in the intensity of the magnetic field.

If the circulation time in the synchrotron 7 is 2 μsec, 10 full turns take 20 μsec. Thereafter, the ion beam injected into the synchrotron 7 is accelerated and the magnetic field of the deflector magnets is intensified to the rated intensity accordingly. After getting to the rated intensity, the ion beam is taken out while it is circulating so as to be utilized typically for cancer therapy, a physical experiment or the like.

On the other hand, the laser ion beam is subjected to multi-turn injection, using the laser ion source 1a in this embodiment. The operation period of the laser ion source 1a depends on the frequency of the laser. If a laser frequency of 20 Hz is used for operation, the ion beam is supplied in every 50 msec. Since the operation of multi-turn injection is conducted by using such beams, the bump electromagnet 12 for ion beam injection is magnetically excited in every 50 msec and ion beams can be injected into the synchrotron 7, shifting the bump trajectory as in the case of conventional techniques.

Multi-turn injection can be realized by controlling the extent of magnetic excitation of the bump electromagnet 12 for each injection. More specifically, the spot at which an ion beam is injected into the synchrotron 7 can be shifted by gradually reducing the amperage of the electric current that is supplied to the bump electromagnet 12 for each injection. As a result, with this arrangement, it is possible to realize multi-turn injection.

The laser frequency can be raised either by operating a single laser ion source 1a until the frequency gets to about 100 Hz or by using a plurality of laser ion sources 1a. In other words, the laser frequency can be raised either by operating a single laser ion source 1a and using a plurality of laser beam sources 20 or by arranging a plurality of laser ion sources 1a.

Thus, this embodiment adopts multi-turn injection using a short pulse high current laser ion source 1a to make it possible to achieve a long circulation time for ion beams. Then, the ratio of the time for ring injection, acceleration and deceleration, which is dead time, relative to the entire operation time can be reduced to improve the ion beam utilization efficiency.

Thus, with this embodiment, it is possible to realize multi-turn injection by controlling the extent of magnetic excitation of the bump electromagnet 12 for ion beam injection. Then, as a result, the amperage of the circulating electric current can be raised to improve the ion beam utilization efficiency.

Second Embodiment

Figure 6:
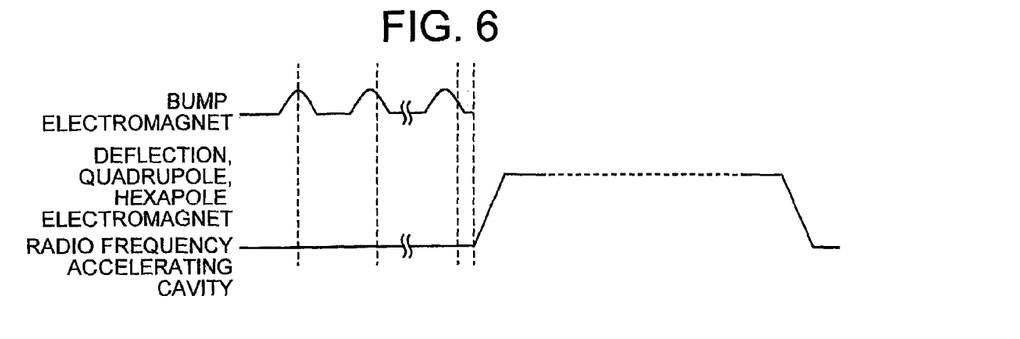
FIG. 6 is a timing chart of the operation of the bump magnet and that of the radio frequency accelerating cavity of the second embodiment of particle accelerator according to the present invention.

FIG. 6 is a timing chart of the operation of the bump magnet and that of the radio frequency accelerating cavity of the second embodiment of particle accelerator according to the present invention. In FIG. 6, the components same as those of the first embodiment are denoted by the same reference symbols and will not be described repeatedly.

As shown in FIG. 6, this embodiment differs from the above described first embodiment in that it employs a different method of controlling the magnetic excitation of the bump electromagnet 12 for ion beam injection. More specifically, the synchrotron/takeout device 15 of this embodiment controls the extent of magnetic excitation of the bump electromagnet 12 so as keep it to a constant level for each and every injection. The timing control unit 16 controls the bump electromagnet 12 so as to make it to be magnetically excited in synchronism with the pulse timing of the laser ion source 1a and subsequently shift the timing of magnetic excitation out of synchronism.

Thus, in this embodiment, the bump electromagnet 12 is magnetically excited in synchronism with the pulse timing of the laser ion source 1a and the magnetic field applied to the ion beam is altered by keeping the extent of magnetic excitation to a constant level and shifting the timing of magnetic excitation.

As described above, multi-turn injection is made possible by keeping the extent of magnetic excitation of the bump electromagnet 12 to a constant level and shifting the timing of magnetic excitation to thereby alter the magnetic field applied to the ion beam. With this arrangement, the amperage of the circulating electric current can be raised to improve the ion beam utilization efficiency.

Other Embodiments

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

For example, the LETB system 2 is provided in each of the above described embodiments, it is not necessary to provide the LETB system 2.

Further, the above configurations of the first embodiment and the second embodiment may be applied not only to the ions but protons.

What is claimed is:

1. A particle accelerator comprising:
a particle source from which a particle beam is extracted with a beam pulse width of not greater than 2 μsec;
a linear accelerator that accelerates the particle beam extracted from the particle source;
a synchrotron that receives the particle beam transported thereto from the linear accelerator and causes the particle beam to circulate in order to accelerate the particle beam until the particle beam gets to a predetermined energy level;
a bump electromagnet that shifts the circulating path of the particle beam each time the particle beam makes a full turn; and
a controller that controls, by gradually reducing the amperage of electric current that is supplied to the bump electromagnet each time the particle beam makes the full turn, extent of magnetic excitation of the bump electromagnet and controls timing of magnetic excitation of the bump electromagnet according to the pulse timing of the particle source.

2. The particle accelerator according to claim 1, wherein the controller controls the bump electromagnet so as to be magnetically excited in synchronism with the pulse timing of the particle source and changes the extent of magnetic excitation of the bump electromagnet.

3. The particle accelerator according to claim 1, wherein the controller controls the extent of magnetic excitation of the bump electromagnet so as to keep it to a constant level and controls the bump electromagnet so as to be magnetically excited in synchronism with the pulse timing of the particle source and subsequently shift the timing of magnetic excitation out of synchronism.

4. The particle accelerator according to claim 1, wherein the linear accelerator includes a radio frequency quadrupole type linear accelerator that electrically converges and accelerates the particle beam, and a drift tube type linear accelerator that electrically accelerates the particle beam.

5. The particle accelerator according to claim 4, wherein the controller synchronizes output timing of the radio frequency quadrupole type linear accelerator and that of the drift tube type linear accelerator with the pulse timing of the particle source.

6. The particle accelerator according to claim 1, wherein the particle beam extracts particles from the particle source for a plurality of times.

7. The particle accelerator according to claim 1, wherein a plurality of the particle sources are arranged.

8. A medical equipment comprising:
a particle source from which a particle beam is extracted with a beam pulse width of not greater than 2 μsec;
a linear accelerator that accelerates the particle beam extracted from the particle source;
a synchrotron that receives the particle beam transported thereto from the linear accelerator and causes the particle beam to circulate in order to accelerate the particle beam until the particle beam gets to a predetermined energy level;
a bump electromagnet that shifts the circulating path of the particle beam each time the particle beam makes a full turn;
a controller that controls, by gradually reducing the amperage of electric current that is supplied to the bump electromagnet each time the particle beam makes the full turn, extent of magnetic excitation of the bump electromagnet and controls timing of magnetic excitation of the bump electromagnet according to pulse timing of the particle source;
a takeout device that takes out the particle beam accelerated by the synchrotron; and
an irradiation device that irradiates the particle beam taken out by the takeout device onto an object of irradiation.

9. A method for a particle accelerator, the method comprising:
extracting a particle beam from a particle source, with a beam pulse width of not greater than 2 μsec;
accelerating, by a linear accelerator, the particle beam extracted from the particle source;
receiving, by a synchrotron, the particle beam transported thereto from the linear accelerator and causing the particle beam to circulate in order to accelerate the particle beam until the particle beam gets to a predetermined energy level;
shifting, by a bump electromagnet, the circulating path of the particle beam each time the particle beam makes a full turn; and
controlling, by a controller, by gradually reducing the amperage of electric current that is supplied to the bump electromagnet each time the particle beam makes the full turn, extent of magnetic excitation of the bump electromagnet and controlling timing of magnetic excitation of the bump electromagnet according to the pulse timing of the particle source.

* * * * *